(12) United States Patent
Brown et al.

(10) Patent No.: US 9,881,776 B2
(45) Date of Patent: Jan. 30, 2018

(54) MONITORING LIQUID CHROMATOGRAPHY ELUTION TO DETERMINE WHEN TO PERFORM A LOCKMASS CALIBRATION

(71) Applicant: Micromass UK Limited, Wilmslow (GB)

(72) Inventors: Jeffery Mark Brown, Hyde (GB); Paul Murray, Manchester (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/313,823

(22) PCT Filed: May 29, 2015

(86) PCT No.: PCT/GB2015/051567
§ 371 (c)(1),
(2) Date: Nov. 23, 2016

(87) PCT Pub. No.: WO2015/181562
PCT Pub. Date: Dec. 3, 2015

(65) Prior Publication Data
US 2017/0186594 A1 Jun. 29, 2017

(30) Foreign Application Priority Data
May 29, 2014 (EP) .................................... 14170506
May 29, 2014 (GB) .................................. 1409554.1

(51) Int. Cl.
*H01J 49/00* (2006.01)
*G01N 30/72* (2006.01)
*G01N 30/86* (2006.01)

(52) U.S. Cl.
CPC ...... *H01J 49/0009* (2013.01); *G01N 30/7266* (2013.01); *G01N 30/8665* (2013.01); *H01J 49/0027* (2013.01)

(58) Field of Classification Search
CPC .............. H01J 49/0009; H01J 49/0027; G01N 30/8665; G01N 30/7266
USPC ........................................ 250/281, 282, 288
See application file for complete search history.

(56) References Cited

U.S. PATENT DOCUMENTS

| 7,047,144 | B2 | 5/2006 | Steiner |
| 7,348,553 | B2 | 3/2008 | Wang et al. |
| 7,476,850 | B2 | 1/2009 | Oonishi et al. |
| 7,518,104 | B2 | 4/2009 | Gabeler |
| 9,177,765 | B2 | 11/2015 | Olney |

(Continued)

FOREIGN PATENT DOCUMENTS

JP S6095346 5/1985

*Primary Examiner* — Michael Maskell
(74) *Attorney, Agent, or Firm* — Womble Bond Dickinson (US) LLP; Deborah M. Vernon; Heath T. Misley (57) ABSTRACT

A method of mass spectrometry is disclosed that comprises acquiring mass spectral data during a single experimental run or acquisition of a mass spectrometer and determining a first time T during the single experimental run or acquisition for calibrating the mass spectrometer. The step of determining the first time T further comprises determining a time when the mass spectral data being acquired during the single experimental run or acquisition is equal to or below a threshold. The mass spectrometer is then calibrated by introducing calibrant or lockmass ions at the first time T.

15 Claims, 2 Drawing Sheets

(56) References Cited

U.S. PATENT DOCUMENTS

| 9,418,824 B2 | 8/2016 | Wildgoose | |
| 2007/0200060 A1* | 8/2007 | Russ, IV | H01J 49/0009 |
| | | | 250/288 |
| 2015/0008310 A1* | 1/2015 | Ledford, Jr. | H01J 49/0009 |
| | | | 250/252.1 |
| 2016/0211125 A1 | 7/2016 | Knochenmuss | |

* cited by examiner

MONITORING LIQUID CHROMATOGRAPHY ELUTION TO DETERMINE WHEN TO PERFORM A LOCKMASS CALIBRATION

CROSS-REFERENCE TO RELATED APPLICATIONS

This application represents the U.S. National Phase of International Application No. PCT/GB2015/051567 entitled "Monitoring Liquid Chromatography Elution to Determine When to Perform a Lockmass Calibration" filed 29 May 2015, which claims priority from and the benefit of United Kingdom patent application No. 1409554.1 filed on 29 May 2014 and European patent application No. 14170506.1 filed on 29 May 2014. The entire contents of these applications areincorporated herein by reference.

FIELD OF THE INVENTION

The present invention relates generally to mass spectrometry and in particular to methods of mass spectrometry and mass spectrometers.

BACKGROUND

During its operation a mass spectrometer may experience changing conditions which can have a significant impact upon the measurements made by the mass analyser. It is well known, for example, that temperature changes can significantly shift the measured mass to charge ratio of ions.

In order to address this problem it is known during operation of a mass spectrometer to periodically calibrate the mass spectrometer, e.g. by periodically mass analysing known lockmass or calibration ions. If the mass spectrometer determines that the measured mass to charge ratio of the known lockmass or calibration ions has shifted (or broadened) then the measured mass to charge ratio of analyte ions may be adjusted to correct for the shift, or the mass spectrometer may be adjusted in some other way.

Mass analysing known lockmass or calibration ions during operation of a mass spectrometer typically involves introducing lockmass or calibration ions into the mass analyser in place of the analyte ions. However, this gives rise to a problem in that the displaced analyte ions are then lost to the system and the analyte ions are not measured by the mass analyser. As a result, portions of the resulting mass spectral data may be degraded and/or lost.

US 2006/169883 (Wang), EP-2741312 (Knochenmuss) and WO 2014/135866 (Micromass) disclose methods for calibrating a mass spectrometer.

It is desired to provide an improved mass spectrometer and method of mass spectrometry.

SUMMARY

According to an aspect there is provided a method of mass spectrometry comprising:

acquiring mass spectral data during a single experimental run or acquisition of a mass spectrometer;

determining a first time T during the single experimental run or acquisition for calibrating the mass spectrometer, wherein the step of determining further comprises determining a time when the mass spectral data being acquired during the single experimental run or acquisition is equal to or below a threshold; and calibrating the mass spectrometer by introducing calibrant or lockmass ions at the first time T.

According to various embodiments the time at which a mass spectrometer is calibrated during an experimental run is determined based on the mass spectral data acquired during the experimental run.

It will be appreciated that the approach according to various embodiments is in contrast with conventional methods wherein the mass spectrometer is calibrated at fixed times during an acquisition and wherein the fixed times are determined in advance before the acquisition (i.e. before mass spectral data is actually acquired). In the known methods, the times are typically set at fixed periodic intervals at which points in time known lockmass or calibration ions are then introduced and mass analysed.

Since the known approach uses fixed periodic intervals which are set before the acquisition of mass spectral data, the time at which the mass spectrometer is calibrated takes no account of any kind of real-time mass spectral information acquired during the experimental run. Certain ions and/or particularly important, useful or interesting analyte ions may only be present during the experimental run for or at particular periods of time. Thus, following the conventional approach, it is possible that mass spectral data and/or particularly important, useful or interesting mass spectral data will be degraded and/or otherwise lost due to the analyte ions of interest being displaced by lockmass or calibration ions.

According to various embodiments, the time T at which the mass spectrometer is calibrated (by introducing lockmass or calibration ions) is determined taking into account real-time mass spectral data i.e. the time at which calibration is performed is in various embodiments based on the mass spectral data being acquired during the current experimental run or acquisition rather than being determined in advance. In particular, the time T at which the mass spectrometer is calibrated (by introducing calibrant or lockmass ions) is determined by determining a time when the mass spectral data is equal to or below a threshold.

This then means that the time T at which calibration is performed can be chosen so as to minimise the degradation of and/or loss of mass spectral data relating to analyte ions of interest. That is, the calibration time T can be chosen so as to avoid times during which analyte ions and/or particularly important, useful or interesting (e.g. particularly abundant) analyte ions are present. The calibration time T can be chosen so as to be at a time when no analyte ions or less important, useful or interesting (e.g. relatively scarce) analyte ions are present.

The approach according to various embodiments is in contrast with the methods disclosed in US 2006/169883 (Wang), EP-2741312 (Knochenmuss) and WO 2014/135866 (Micromass) which do not disclose the concept of introducing calibrant or lockmass ions when it is determined that acquired mass spectral data (e.g. the total ion current or one or more ion intensities) is equal to or below a threshold.

It will therefore be appreciated that the approach according to various embodiments can avoid the degradation and/or loss (or at least minimise) the degree to which mass spectral data of potential interest is degraded and/or lost due to the calibration of a mass spectrometer during an experimental run.

According to an embodiment, the single experimental run or acquisition is carried out between a second time t2 and a third time t3, and wherein $t2 < T < t3$.

According to an embodiment, the single experimental run or acquisition of the mass spectrometer comprises a single gas chromatography or liquid chromatography run.

According to an embodiment, the method may further comprise:

setting a provisional time $T_0$ during the single experimental run or acquisition for calibrating the mass spectrometer;

wherein the step of determining the first time T for calibrating the mass spectrometer comprises determining, at or before the provisional time $T_0$, whether the mass spectral data being acquired during the single experimental run or acquisition is equal to or below the threshold;

wherein if the mass spectral data being acquired during the single experimental run or acquisition is determined to be equal to or below the threshold, then the method further comprises calibrating the mass spectrometer at the provisional time so that $T=T_0$; and wherein if the mass spectral data being acquired during the single experimental run or acquisition is determined to be other than equal to or below the threshold, then the method further comprises calibrating the mass spectrometer after the provisional time so that $T>T_0$.

According to an embodiment, calibrating the mass spectrometer after the provisional time so that $T>T_0$ comprises calibrating the mass spectrometer as soon as the mass spectral data being acquired during the single experimental run or acquisition is determined to be equal to or below the threshold.

According to an embodiment, the step of determining the first time T for calibrating the mass spectrometer further comprises determining a time when the mass spectral data being acquired during the single experimental run or acquisition is increasing, constant or decreasing.

According to an embodiment, the determination is made based on a current value of the mass spectral data being acquired during the single experimental run or acquisition.

According to an embodiment, the determination is made based on data derived from the mass spectral data acquired during the single experimental run or acquisition.

According to an embodiment, the mass spectral data acquired during the single experimental run or acquisition comprises total ion current ("TIC").

According to an embodiment, the mass spectral data acquired during the single experimental run or acquisition comprises one or more ion intensities.

According to an embodiment, calibrating the mass spectrometer further comprises mass analysing the calibrant or lockmass ions.

According to an embodiment, calibrating the mass spectrometer comprises mass analysing the calibrant or lockmass ions in place of analyte ions.

According to an embodiment, the method further comprises calibrating the mass spectrometer a plurality of times during the single experimental run or acquisition.

According to another aspect there is provided a mass spectrometer comprising:

a control system arranged and adapted:

(i) to cause the mass spectrometer to acquire mass spectral data during a single experimental run or acquisition of the mass spectrometer;

(ii) to determine a first time T during the single experimental run or acquisition for calibrating the mass spectrometer by determining a time when the mass spectral data acquired during the single experimental run or acquisition is equal to or below a threshold; and (iii) to calibrate the mass spectrometer by introducing calibrant or lockmass ions at the first time T.

According to an aspect there is provided a method of mass spectrometry comprising:

acquiring mass spectral data during a single experimental run or acquisition of a mass spectrometer;

determining a first time T during the single experimental run or acquisition for calibrating the mass spectrometer, wherein the determination is made based on the mass spectral data acquired during the single experimental run or acquisition; and calibrating the mass spectrometer at the first time T.

According to an embodiment, the single experimental run or acquisition is carried out between a second time $t_2$ and a third time $t_3$, wherein $t_2<T<t_3$.

According to an embodiment, the single experimental run or acquisition of the mass spectrometer comprises a single gas chromatography or liquid chromatography run.

According to an embodiment, the step of determining the first time T for calibrating the mass spectrometer comprises determining a time when the mass spectral data acquired during the single experimental run or acquisition meets one or more conditions.

According to an embodiment, the method further comprises:

setting a provisional time $T_0$ during the single experimental run or acquisition for calibrating the mass spectrometer;

wherein the step of determining the first time T for calibrating the mass spectrometer comprises determining, at or before the provisional time $T_0$, whether the mass spectral data acquired during the single experimental run or acquisition meets one or more conditions;

wherein if the mass spectral data acquired during the single experimental run or acquisition is determined to meet the one or more conditions, then the method further comprises calibrating the mass spectrometer at the provisional time so that $T=T_0$; and wherein if the mass spectral data acquired during the single experimental run or acquisition is determined not to meet the one or more conditions, then the method further comprises calibrating the mass spectrometer after the provisional time so that $T>T_0$.

According to an embodiment, calibrating the mass spectrometer after the provisional time so that $T>T_0$ comprises calibrating the mass spectrometer as soon as the mass spectral data acquired during the single experimental run or acquisition is determined to meet the one or more conditions.

According to an embodiment, the mass spectral data acquired during the single experimental run or acquisition is determined to meet one of the one or more conditions if the mass spectral data acquired during the single experimental run or acquisition is above, equal to or below a threshold.

According to an embodiment, the mass spectral data acquired during the single experimental run or acquisition is determined to meet one of the one or more conditions if the mass spectral data acquired during the single experimental run or acquisition is increasing, constant or decreasing.

According to an embodiment, the determination is made based on a current value of the mass spectral data acquired during the single experimental run or acquisition.

According to an embodiment, the determination is made based on data derived from the mass spectral data acquired during the single experimental run or acquisition.

According to an embodiment, the mass spectral data acquired during the single experimental run or acquisition comprises total ion current ("TIC").

According to an embodiment, the mass spectral data acquired during the single experimental run or acquisition comprises one or more ion intensities.

According to an embodiment, calibrating the mass spectrometer comprises mass analysing calibrant or lockmass ions.

According to an embodiment, calibrating the mass spectrometer further comprises mass analysing the calibrant or lockmass ions in place of analyte ions.

According to an embodiment, the method further comprises calibrating the mass spectrometer a plurality of times during the single experimental run or acquisition.

According to another aspect there is provided a mass spectrometer comprising:

a control system arranged and adapted:

(i) to cause the mass spectrometer to acquire mass spectral data during a single experimental run or acquisition of the mass spectrometer;

(ii) to determine a first time T during the single experimental run or acquisition for calibrating the mass spectrometer, wherein the determination is based on the mass spectral data acquired during the single experimental run or acquisition; and (iii) to calibrate the mass spectrometer at the first time T.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) C60 vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenylanthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments together with other arrangements given for illustrative purposes only will now be described, by way of example only, and with reference to the accompanying drawings in which.

DETAILED DESCRIPTION

A conventional approach to calibrating a mass spectrometer will first be described.

According to a known method of calibrating a mass spectrometer, a mass spectrometer is calibrated at fixed predetermined times during its operation during an experimental run or acquisition. The fixed times are predetermined before the experimental run or acquisition is begun i.e. before any mass spectral data is acquired. The fixed times are typically fixed periodic intervals during the operation of the mass spectrometer at which times the measured mass to charge ratio of known lockmass or calibration ions is then measured.

Calibrating a mass spectrometer using lockmass or calibration ions typically involves introducing lockmass or calibration ions into the mass analyser in place of the analyte ions and mass analysing the lockmass or calibration ions. The displaced analyte ions are lost to the system and are not measured by the mass analyser.

For example, when performing a liquid chromatography mass spectrometry ("LCMS") experiment, the mass spectrometer is typically calibrated at fixed intervals during the liquid chromatography ("LC") run by interrupting the flow of analyte into the instrument, sampling known reference (lockmass) ions and then determining whether there is any drift in the calibration accuracy. To do this, the mass spectrometer is usually set before the experiment to switch between an Electrospray ion source and a lock spray for short periods at fixed predetermined intervals during the liquid chromatography run.

Since the known methods use fixed periodic intervals which are predetermined before the operation of the mass spectrometer, the time at which the mass spectrometer is calibrated does not take into account any kind of real-time mass spectral information such as what compounds are eluting from the liquid chromatography device. The width of some chromatographic peaks produced by certain analyte components (species) eluting from a liquid chromatography column may be relatively narrow and it can be the case that these relatively narrow peaks (or other peaks) may either be partially or completely missed if the instrument interrupts the analysis to perform a lockmass calibration at the point in time when the component reaches the Electrospray ion source.

Thus, in the known methods, it is possible that particularly important, useful or interesting analyte ions will be displaced by lockmass or calibration ions. Accordingly, significant mass spectral data may be degraded and/or lost.

Figure 1A:
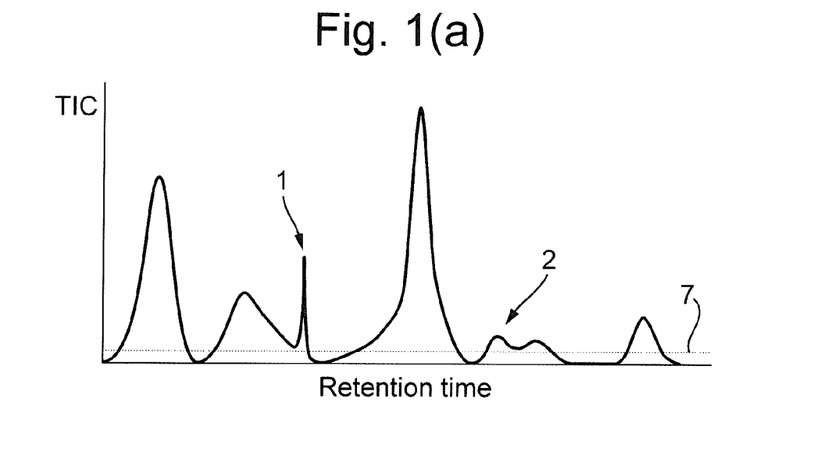
FIG. 1A shows an example Total Ion Current ("TIC") chromatogram.
Figure 1B:
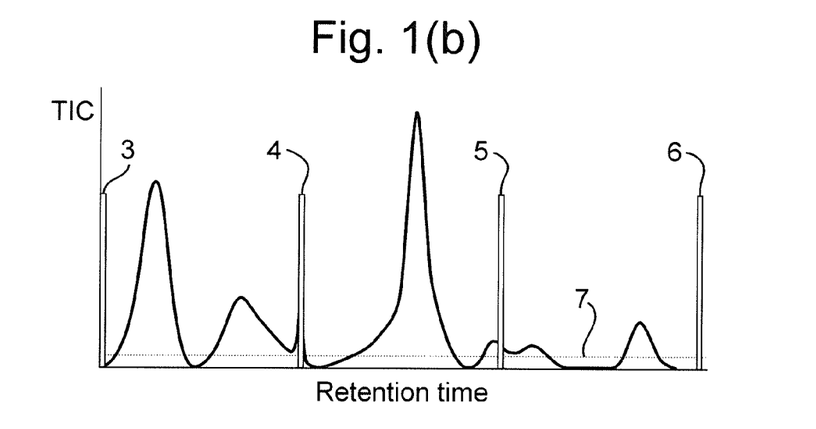
FIG. 1B shows an example chromatogram that would result from the chromatogram of FIG. 1A with the introduction of fixed period lockmass ions in a conventional manner.
Figure 1C:
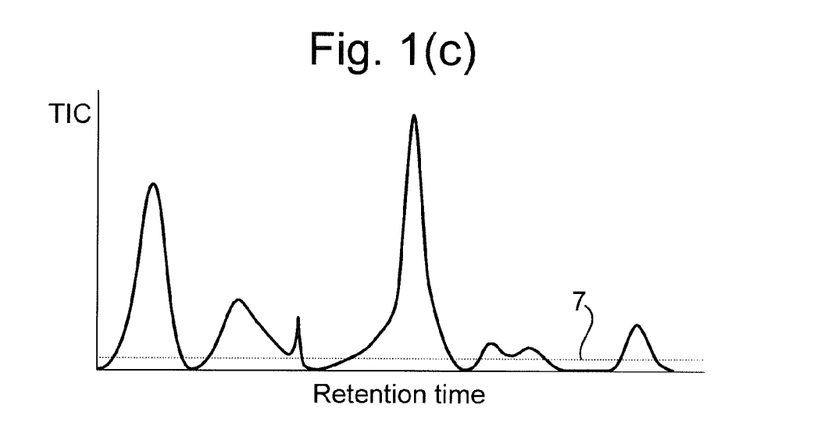
FIG. 1C shows an example chromatogram that would result from the chromatogram of FIG. 1A after removal of the fixed period lockmass ions of FIG. 1B.

FIGS. 1A-C illustrates in more detail the problem with the known approach.

FIG. 1A shows an example chromatogram for a sample eluting from a chromatography device and being ionised by an ion source. The chromatogram depicted in FIG. 1A plots the evolution of the total ion current ("TIC") with retention time. A number of chromatographic peaks are present in the chromatogram at different retention times. Each peak results from a particular component of the sample being analysed.

The chromatographic peaks have various different retention times, widths and intensities which, as is known in the art, depend on the properties of the particular component. FIG. 1A shows in particular one chromatographic peak 1 having a relatively narrow retention time width and another chromatographic peak 2 that has a particularly low intensity.

FIG. 1B shows an example TIC chromatogram where lockmass or calibration ions are periodically introduced to the mass analyser in place of the analyte ions in accordance with the known approach. Four chromatographic peaks 3,4,5,6 are present in the chromatogram corresponding to lockmass or calibration ions being periodically introduced to the mass analyser four times at regular predetermined intervals.

As can be seen from FIG. 1B, one of the lockmass ion chromatographic peaks 4 (accidently) coincides with the relatively narrow analyte chromatographic peak 1 and another of the lockmass peaks 5 coincides with the relatively low intensity analyte peak 2. This is the result of lockmass or calibration ions being introduced into the mass analyser at times when the analyte ions that produce chromatographic peaks 1,2 would otherwise have been introduced. It will be appreciated that this can happen in the known approach because the times at which the lockmass ions are introduced into the mass analyser (i.e. the times at which the mass spectrometer is calibrated) are fixed and predetermined before the mass spectral data is acquired.

As a result of the overlap, less mass spectral data will be acquired for the ions that produced the low intensity peak 2 while no data at all will be acquired for the ions that produced the narrow peak 1. An example of this effect is shown in FIG. 1C where the narrow chromatographic peak 1 is not present in the final measured mass chromatogram.

It should be noted that in this example the effect of the other two lockmass peaks 3 6 is minimal because they coincide with regions of the chromatogram at which very few ions are present e.g. where the TIC is below a threshold 7.

It can therefore be seen that according to the known approach, mass spectral data can be degraded and/or lost as a result of calibrating the mass spectrometer at fixed predetermined times.

An embodiment will now be described.

According to various embodiments the time(s) at which the mass spectrometer is calibrated takes into account the real-time mass spectral data i.e. the mass spectrometer is calibrated at time(s) which are based on the mass spectral data acquired during the current experimental run or acquisition.

The calibration time may be chosen so as to avoid times when analyte ions and/or particularly important, useful or interesting (e.g. particularly abundant) analyte ions are present. For example, the calibration time may be chosen to be at a time when no analyte ions or when less important, less useful or less interesting analyte ions are present.

According to one embodiment, the analyte (e.g. eluting from an liquid chromatography device) may be monitored in order to determine when a lockmass calibration can be performed without missing the acquisition of significant spectra.

For example, by allowing the mass spectrometer to monitor the TIC and by pre-defining a threshold level 7, the instrument can determine a time at which to calibrate e.g. the instrument can determine a time at which to switch to introducing reference calibration (lockmass) ions, optionally from a second ion source. In this way, the problem of the instrument switching to a lockmass calibration during the middle of a chromatographic peak and the resultant loss of relevant data can be addressed.

According to an embodiment, the instrument may be configured to perform a lockmass calibration at fixed intervals conditional that the TIC at the time is at a level below the defined threshold 7. Otherwise the lockmass calibration may be delayed until such time that the TIC falls below the required threshold 7.

Figure 2A:
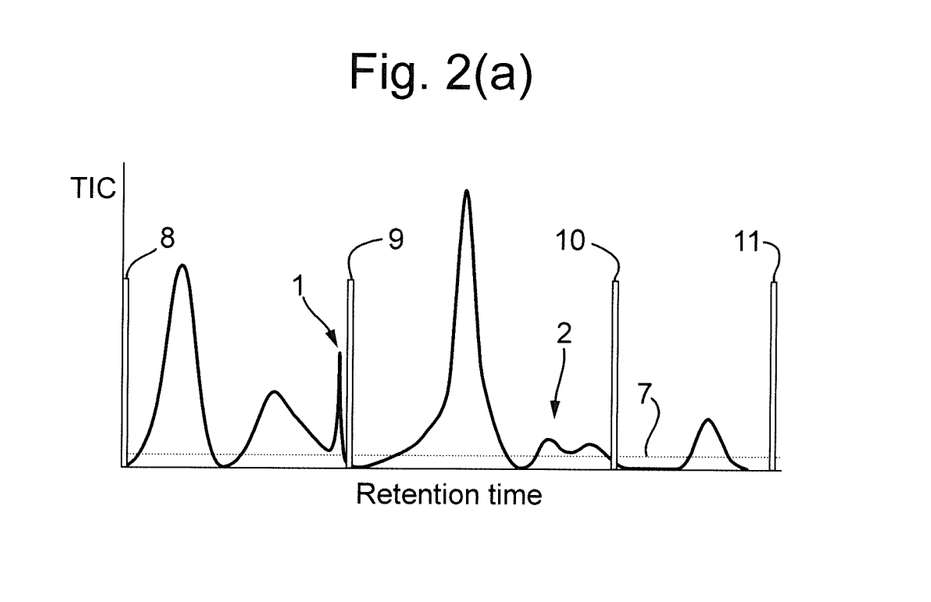
FIG. 2A shows an example chromatogram that would result from the chromatogram of FIG. 1A with the introduction of lockmass ions whose timing is threshold dependent according to an embodiment and FIG. 2B shows an example chromatogram according to an embodiment that would result from the chromatogram of FIG. 1A after removal of the threshold dependent lockmass ions of FIG. 2A.
Figure 2B:
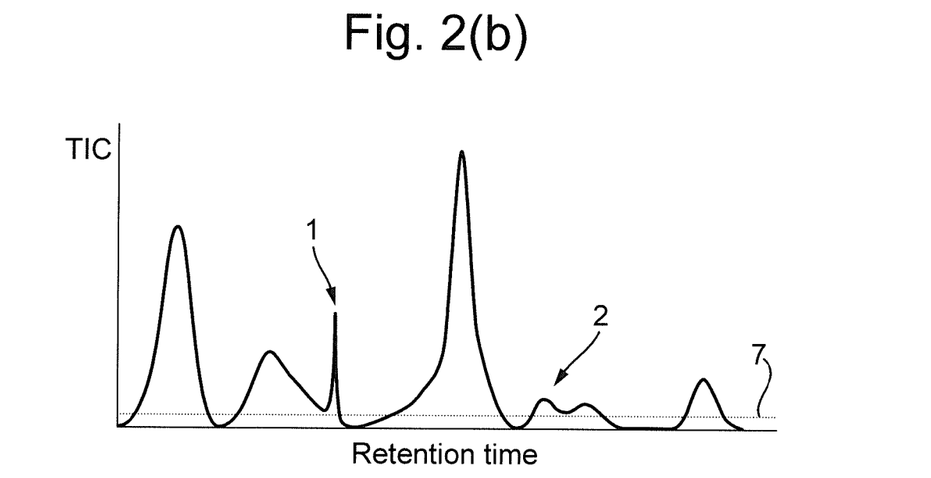

An example of this embodiment is illustrated in FIGS. 2A-B.

FIG. 2A shows the example chromatogram of FIG. 1A together with four lockmass peaks 8,9,10,11 according to an embodiment. In contrast with FIG. 1B, the timings at which the calibrations are performed according to an embodiment and as shown in FIG. 2A are dependent on the mass spectral data and in particular are dependent on the real time (i.e. current) value of the TIC. According to this embodiment, the mass spectrometer may be initially set to perform calibration routines at fixed times e.g. corresponding to the fixed times of peaks 3,4,5,6 of FIG. 1B. The mass spectrometer may also be configured to monitor a current value of the mass spectral data (e.g. the TIC).

If, at or just before one of the fixed times, the value of the TIC is below a threshold 7 then the mass spectrometer according to an embodiment proceeds to perform the calibration routine at the fixed time. However, if at or just before one of the fixed times the value of the TIC is above the threshold 7 then calibration may be delayed until e.g. the TIC has dropped below the threshold 7.

Thus, as can be seen from FIG. 2A, the timings of lockmass peaks 8 and 11 correspond to the timings of lockmass peaks 3 and 6 shown in FIG. 1B because the value of the TIC at the times of these peaks is below the threshold 7. The timings of peaks 9 and 10 are, however, shifted with respect to peaks 4 and 5 as shown in FIG. 1B i.e. peaks 9,10 are delayed until the TIC drops below the threshold 7.

The resulting measured mass chromatogram i.e. after removal of the lockmass peaks, is shown in FIG. 2B. When compared with FIG. 1C it can be seen that the narrow peak 1 is present in the chromatogram and the low intensity peak 2 has not been degraded.

It will be appreciated that according to various embodiments, the degradation and/or loss of mass spectral data can advantageously be avoided or at least the degree to which the mass spectral data is degraded and/or lost can be minimised. In particular, the problem of particularly important, useful or interesting (e.g. particularly abundant) analyte ions being displaced by lockmass ions can be avoided.

According to an embodiment, the instrument may be configured so as to only perform a calibration when the mass spectral data is increasing or decreasing. For example, in an embodiment, the instrument may be configured so that the calibration (lockmass correction) is only performed on the falling edge of an eluting peak e.g. once the TIC has fallen below a threshold 7 intensity.

According to another embodiment, instead of monitoring the TIC, the intensity of one or more ion species of interest may be monitored.

It will be appreciated that monitoring the TIC or targeted ion intensity in accordance with various embodiments reduces the chance of relevant information being missed during the calibration of the mass spectrometer with lockmass or calibration ions.

Embodiments are applicable to both gas chromatography ("GC") and liquid chromatography ("LC") acquisitions.

Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry comprising:
   acquiring mass spectral data during a single experimental run or acquisition of a mass spectrometer;
   during said single experimental run or acquisition, determining a first time T for calibrating said mass spectrometer, wherein said first time T is during said single experimental run or acquisition, wherein the step of determining said first time T comprises determining a time when said mass spectral data being acquired during said single experimental run or acquisition is equal to or below a threshold; and
   calibrating said mass spectrometer by introducing calibrant or lockmass ions at said first time T.

2. A method as claimed in claim 1, wherein said single experimental run or acquisition is carried out between a second time $t_2$ and a third time $t_3$, and wherein $t_2<T<t_3$.

3. A method as claimed in claim 1, wherein said single experimental run or acquisition of said mass spectrometer comprises a single gas chromatography or liquid chromatography run.

4. A method as claimed in claim 1, further comprising:
   setting a provisional time $T_0$ during said single experimental run or acquisition for calibrating said mass spectrometer;
   wherein said step of determining said first time T for calibrating said mass spectrometer comprises determining, at or before said provisional time $T_0$, whether said mass spectral data being acquired during said single experimental run or acquisition is equal to or below said threshold;
   wherein if said mass spectral data being acquired during said single experimental run or acquisition is determined to be equal to or below said threshold, then said method further comprises calibrating said mass spectrometer at said provisional time so that $T=T_0$; and
   wherein if said mass spectral data being acquired during said single experimental run or acquisition is determined to be other than equal to or below said threshold, then said method further comprises calibrating said mass spectrometer after said provisional time so that $T>T_0$.

5. A method as claimed in claim 4, wherein calibrating said mass spectrometer after said provisional time so that $T>T_0$ comprises calibrating said mass spectrometer as soon as said mass spectral data being acquired during said single experimental run or acquisition is determined to be equal to or below said threshold.

6. A method as claimed in claim 1, wherein said step of determining said first time T for calibrating said mass spectrometer further comprises determining a time when said mass spectral data being acquired during said single experimental run or acquisition is increasing, constant or decreasing.

7. A method as claimed in claim 1, wherein said determination is made based on a current value of said mass spectral data being acquired during said single experimental run or acquisition.

8. A method as claimed in claim 1, wherein said determination is made based on data derived from said mass spectral data acquired during said single experimental run or acquisition.

9. A method as claimed in claim 1, wherein said mass spectral data acquired during said single experimental run or acquisition comprises total ion current ("TIC").

10. A method as claimed in claim 1, wherein said mass spectral data acquired during said single experimental run or acquisition comprises one or more ion intensities.

11. A method as claimed in claim 1, wherein the step of calibrating said mass spectrometer further comprises mass analysing said calibrant or lockmass ions.

12. A method as claimed in claim 11, wherein the step of calibrating said mass spectrometer further comprises mass analysing said calibrant or lockmass ions in place of analyte ions.

13. A method as claimed in claim 1, further comprising calibrating said mass spectrometer a plurality of times during said single experimental run or acquisition.

14. A mass spectrometer comprising:
a control system arranged and adapted:
(i) to cause said mass spectrometer to acquire mass spectral data during a single experimental run or acquisition of said mass spectrometer;
(ii) during said single experimental run or acquisition, to determine a first time T for calibrating said mass spectrometer, wherein said first time T is during said single experimental run or acquisition, by determining a time when said mass spectral data being acquired during said single experimental run or acquisition is equal to or below a threshold; and
(iii) to calibrate said mass spectrometer by introducing calibrant or lockmass ions at said first time T.

15. A method of mass spectrometry comprising:
acquiring mass spectral data during a single experimental run or acquisition of a mass spectrometer;
determining a first time T during said single experimental run or acquisition for calibrating said mass spectrometer, wherein the step of determining further comprises determining a time when said mass spectral data being acquired during said single experimental run or acquisition is equal to or below a threshold; and
calibrating said mass spectrometer by introducing calibrant or lockmass ions at said first time T;
the method further comprising:
setting a provisional time $T_0$ during said single experimental run or acquisition for calibrating said mass spectrometer;
wherein said step of determining said first time T for calibrating said mass spectrometer comprises determining, at or before said provisional time $T_0$, whether said mass spectral data being acquired during said single experimental run or acquisition is equal to or below said threshold;
wherein if said mass spectral data being acquired during said single experimental run or acquisition is determined to be equal to or below said threshold, then said method further comprises calibrating said mass spectrometer at said provisional time so that $T=T_0$; and
wherein if said mass spectral data being acquired during said single experimental run or acquisition is determined to be other than equal to or below said threshold, then said method further comprises calibrating said mass spectrometer after said provisional time so that $T>T_0$.

* * * * *